United States Patent
Kiers et al.

(10) Patent No.: US 7,911,612 B2
(45) Date of Patent: Mar. 22, 2011

(54) INSPECTION METHOD AND APPARATUS, LITHOGRAPHIC APPARATUS, LITHOGRAPHIC PROCESSING CELL AND DEVICE MANUFACTURING METHOD

(75) Inventors: Antoine Gaston Marie Kiers, Veldhoven (NL); Arie Jeffrey Den Boef, Waalre (NL); Maurits Van Der Schaar, Eindhoven (NL)

(73) Assignee: ASML Netherlands B.V., Veldhoven (NL)

( * ) Notice: Subject to any disclaimer, the term of this patent is extended or adjusted under 35 U.S.C. 154(b) by 405 days.

(21) Appl. No.: 11/808,922

(22) Filed: Jun. 13, 2007

(65) Prior Publication Data
US 2008/0311344 A1    Dec. 18, 2008

(51) Int. Cl.
*G01B 11/00* (2006.01)
*G03F 9/00* (2006.01)
*G03C 5/00* (2006.01)
*H01L 21/76* (2006.01)

(52) U.S. Cl. ............ 356/399; 356/401; 430/22; 430/30; 438/401

(58) Field of Classification Search ........................ None
See application file for complete search history.

(56) References Cited

U.S. PATENT DOCUMENTS

| | | | |
|---|---|---|---|
| 5,703,692 A | 12/1997 | McNeil et al. | 356/445 |
| 5,805,290 A * | 9/1998 | Ausschnitt et al. | 356/401 |
| 5,880,838 A | 3/1999 | Marx et al. | 356/351 |
| 5,963,329 A | 10/1999 | Conrad et al. | 356/372 |
| 6,433,878 B1 | 8/2002 | Niu et al. | |
| 6,608,690 B2 | 8/2003 | Niu et al. | 356/635 |
| 6,699,624 B2 | 3/2004 | Niu et al. | 430/5 |
| 6,704,661 B1 | 3/2004 | Opsal et al. | 702/27 |
| 6,721,691 B2 | 4/2004 | Bao et al. | 702/189 |
| 6,738,138 B2 | 5/2004 | Wei | 356/369 |
| 6,753,961 B1 | 6/2004 | Norton et al. | 356/364 |
| 6,765,282 B2 * | 7/2004 | Schulz | 257/629 |
| 6,767,680 B2 * | 7/2004 | Schulz | 430/30 |
| 6,768,983 B1 | 7/2004 | Jakatdar et al. | 706/46 |
| 6,772,084 B2 | 8/2004 | Bischoff et al. | 702/127 |

(Continued)

FOREIGN PATENT DOCUMENTS

JP    2001-093820 A    4/2001

(Continued)

OTHER PUBLICATIONS

"Interferometric Method of Checking the Overlay Accuracy in Photolitho Graphic Exposure Processes," Mar. 1, 1990, IBM Technical Disclosure Bulletin, vol. 32, Issue No. 10B, pp. 214-217.*

(Continued)

*Primary Examiner* — Tarifur Chowdhury
*Assistant Examiner* — Gordon J Stock, Jr.
(74) *Attorney, Agent, or Firm* — Sterne, Kessler, Goldstein & Fox P.L.L.C.

(57) ABSTRACT

An overlay target on a substrate is disclosed, the overlay target including a periodic array of structures wherein every $n^{th}$ structure is different from the rest of the structures. The periodic array is desirably made of two interlaced gratings, one of the gratings having a different pitch from the other grating in order to create an asymmetry in the array. This asymmetry can then be measured by measuring the diffraction spectra of radiation reflected from the overlay target. Variation in the asymmetry indicates the presence of an overlay error in layers on the substrate, where overlay targets are printed on subsequent layers.

32 Claims, 11 Drawing Sheets

U.S. PATENT DOCUMENTS

| | | | |
|---|---|---|---|
| 6,785,638 B2 | 8/2004 | Niu et al. | 702/189 |
| 6,804,005 B2 * | 10/2004 | Bischoff et al. | 356/369 |
| 6,813,034 B2 | 11/2004 | Rosencwaig et al. | 356/601 |
| 6,819,426 B2 | 11/2004 | Sezginer et al. | 356/401 |
| 6,855,464 B2 * | 2/2005 | Niu et al. | 430/5 |
| 6,856,408 B2 | 2/2005 | Raymond | 356/601 |
| 6,919,964 B2 | 7/2005 | Chu | 356/601 |
| 6,928,628 B2 | 8/2005 | Seligson et al. | 716/4 |
| 6,972,852 B2 | 12/2005 | Opsal et al. | 356/625 |
| 6,974,962 B2 | 12/2005 | Brill et al. | 250/548 |
| 6,987,572 B2 | 1/2006 | Lakkapragada et al. | 356/601 |
| 7,046,376 B2 | 5/2006 | Sezginer | 356/601 |
| 7,061,615 B1 | 6/2006 | Lowe-Webb | 356/401 |
| 7,061,623 B2 | 6/2006 | Davidson | 356/497 |
| 7,061,627 B2 | 6/2006 | Opsal et al. | 356/601 |
| 7,068,363 B2 | 6/2006 | Bevis et al. | 356/237.5 |
| 7,075,639 B2 * | 7/2006 | Adel et al. | 356/237.5 |
| 7,099,010 B2 * | 8/2006 | Schulz | 356/401 |
| 7,151,594 B2 | 12/2006 | Den Boef et al. | |
| 7,403,259 B2 | 7/2008 | Kruijswijk et al. | |
| 7,481,579 B2 | 1/2009 | Yokhin et al. | |
| 7,528,931 B2 | 5/2009 | Modderman | |
| 7,616,313 B2 | 11/2009 | Kandel et al. | |
| 7,656,528 B2 | 2/2010 | Abdulhalim et al. | |
| 7,663,753 B2 * | 2/2010 | Mieher et al. | 356/401 |
| 2003/0044702 A1 | 3/2003 | Schulz | |
| 2004/0061857 A1 * | 4/2004 | Abdulhalim et al. | 356/400 |
| 2004/0109165 A1 | 6/2004 | Fay et al. | 356/508 |
| 2004/0119970 A1 | 6/2004 | Dusa et al. | 356/237.1 |
| 2004/0137341 A1 * | 7/2004 | Niu et al. | 430/5 |
| 2006/0033921 A1 | 2/2006 | Den Boef et al. | 356/446 |
| 2006/0066855 A1 | 3/2006 | Den Boef et al. | 356/401 |
| 2006/0126074 A1 | 6/2006 | Van Der Werf et al. | 356/489 |
| 2006/0139592 A1 | 6/2006 | Den Boef et al. | 355/53 |
| 2008/0002213 A1 * | 1/2008 | Weiss | 356/620 |
| 2008/0239318 A1 * | 10/2008 | Den Boef et al. | 356/369 |

FOREIGN PATENT DOCUMENTS

| | | |
|---|---|---|
| JP | 2002-311564 A | 10/2002 |
| JP | 2003-068639 A | 3/2003 |
| JP | 2004-200680 A | 7/2004 |
| JP | 2004-519716 A | 7/2004 |
| JP | 2004-533114 A | 10/2004 |
| JP | 2005-142576 A | 6/2005 |
| JP | 2006-179906 A | 7/2006 |
| JP | 2007-305971 A | 11/2007 |
| JP | 2009-532862 A | 9/2009 |
| KR | 2005110467 A * | 11/2005 |

OTHER PUBLICATIONS

English Language Abstract for JP 2001-093820 A, published Apr. 6, 2001; 1 page.

English Language Abstract for JP 2002-311564 A, published Oct. 23, 2002; 1 page.

English Language Description and Claims for JP 2004-519716 A, published Jul. 2, 2004; 5 pages.

English Language Abstract for JP 2004-200680 A, published Jul. 15, 2004; 1 page.

English Language Abstract for JP 2005-142576 A, published Jun. 2, 2005; 1 page.

English Language Abstract for JP 2006-179906 A, published Jul. 6, 2006; 1 page.

English Language Abstract for JP 2007-305971 A, published Nov. 22, 2007; 1 page.

English Translation of Notice of Reasons for Rejection directed to related Japanese Patent application No. 2008-148757, mailed on Jan. 5, 2011, from the Japanese Patent Office; 4 pages.

* cited by examiner

Fig. 4
Fig. 4a
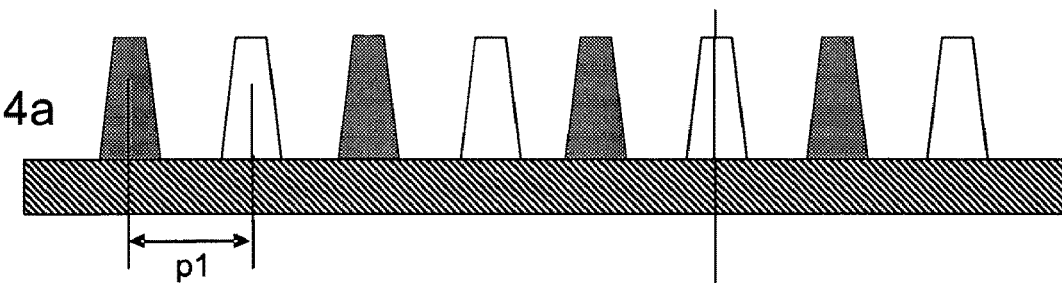
Fig. 4b
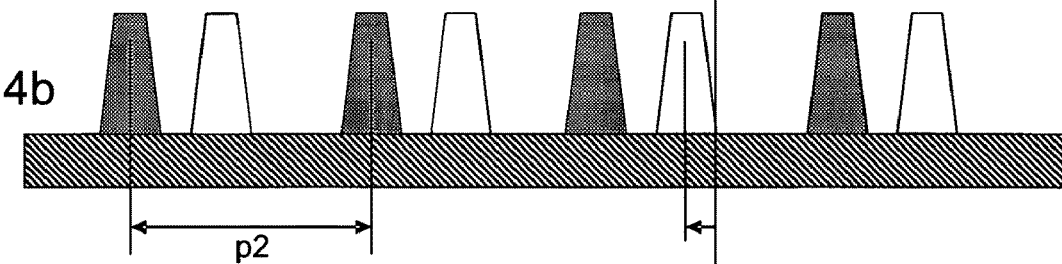
Fig. 4c
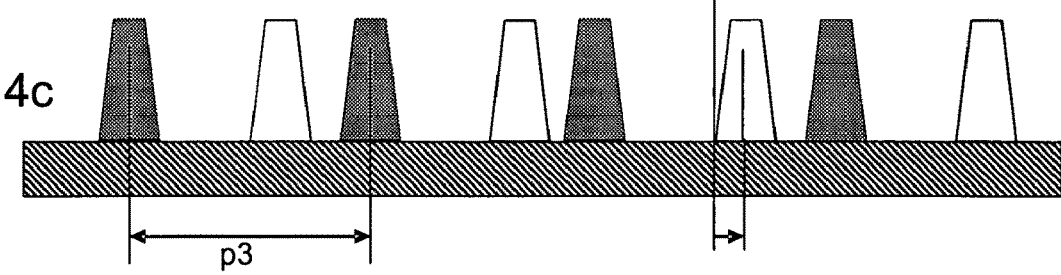

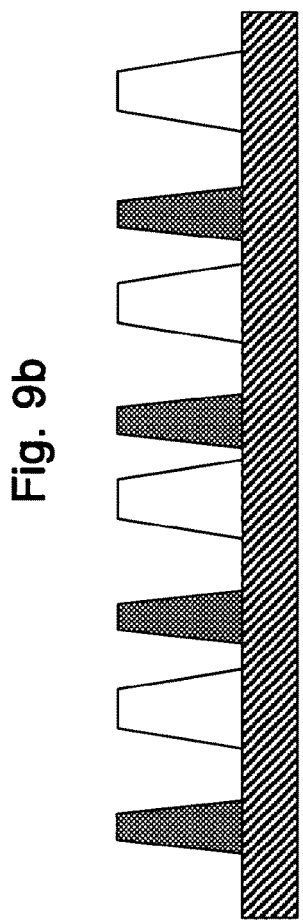
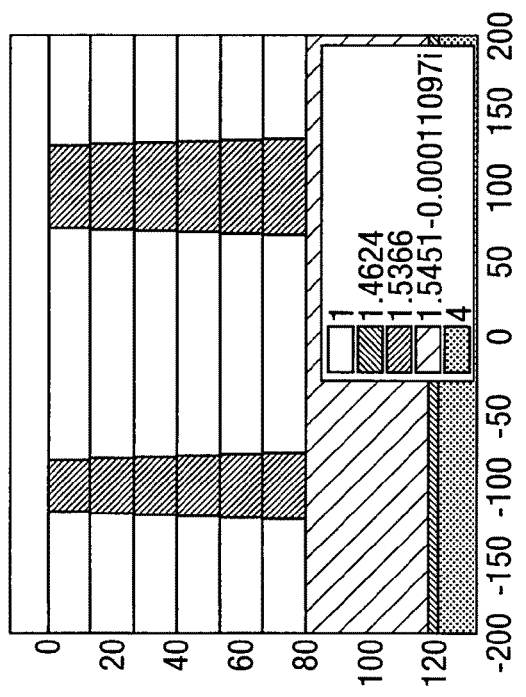
Fig. 9a
Fig. 9b

INSPECTION METHOD AND APPARATUS, LITHOGRAPHIC APPARATUS, LITHOGRAPHIC PROCESSING CELL AND DEVICE MANUFACTURING METHOD

FIELD

The present invention relates to a method of inspection usable, for example, in the manufacture of devices by lithographic techniques and to a method of manufacturing devices using lithographic techniques.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. comprising part of, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"—direction) while synchronously scanning the substrate parallel or anti-parallel to this direction. It is also possible to transfer the pattern from the patterning device to the substrate by imprinting the pattern onto the substrate.

In order to monitor the lithographic process, one or more parameters of the patterned substrate are typically measured, for example the overlay error between successive layers formed in or on the substrate. There are various techniques for making measurements of the microscopic structures formed in a lithographic process, including the use of a scanning electron microscope and various specialized tools. One form of specialized inspection tool is a scatterometer in which a beam of radiation is directed onto a target on the surface of the substrate and one or more properties of the scattered or reflected beam are measured. By comparing one or more properties of the beam before and after it has been reflected or scattered by the substrate, one or more properties of the substrate may be determined. This may be done, for example, by comparing the reflected beam with data stored in a library of known measurements associated with a known substrate property. Two main types of scatterometer are known. A spectroscopic scatterometer directs a broadband radiation beam onto the substrate and measures the spectrum (intensity as a function of wavelength) of the radiation scattered into a particular narrow angular range. An angularly resolved scatterometer uses a set of monochromatic radiation beams and measures the intensity (or intensity ratio and phase difference in case of an ellipsometric configuration) of the scattered radiation as a function of angle. Alternatively, measurement signals of different wavelengths may be measured separately and combined at an analysis stage. The broadband radiation beam will hereinafter be referred to as the measurement beam.

The targets that are used by the scatterometers are generally positioned on portions of a substrate that will not be used for an ultimate product (such as, for instance, the IC). In order to maximize the area available for the product, the target areas are generally limited to "scribe lanes" which are areas of the substrate that will subsequently be sawn or cut to create the separate products.

SUMMARY

It is therefore desirable that the targets fit into these scribe lanes. Smaller and smaller targets are possible with the improvement of etching, printing and other lithographic techniques. However, there is a size limit of the targets that is not limited by printing and like techniques, but by the wavelength of the measurement beam that will eventually be directed onto the target. Targets are often in the form of gratings, which may be one-dimensional rows of bars or two-dimensional arrays of square- or other-shaped structures. The minimum size for these targets is a size at which the pitch (i.e. the distance from one bar or structure to the next) of a grating is smaller than the wavelength of the measurement beam. If the pitch of the grating is smaller than the wavelength of the measurement beam, the first (and higher) diffraction orders of the diffracted radiation beam will lie outside the range of orders detectable by a scatterometer detector (or camera). The range of the diffracted beam that can be measured is limited by the size of the numerical aperture of the optics of the scatterometer. If the first and higher orders are not captured, only the zeroth order will be captured. However, the zeroth order might not have sufficient contrast in its image for meaningful measurements to be obtained. If the patterns are big enough, the zeroth order will contain sufficient information. As the patterns and pitches get smaller, the availability of the higher orders boosts the signal-to-noise ratio.

FIG. 4 shows an attempt to solve this problem according to the state of the art.

FIG. 4A shows a double patterning technique that is used to print small pitches. For example, two identical interlaced gratings, each having a pitch of 90 nm, give rise to an effective grating with a pitch of 45 nm (½ of 90 nm) because the effective pitch is the length of one repeated pattern and in this case, the repeated pattern is a single bar. This smaller effective pitch is depicted as pitch p1 in FIG. 4A. This requires that the interlacing of the gratings be such that the bars of the second grating, shown as the unshaded grating, are exactly centered between the bars of the first, shaded grating.

When the centering of one grating with respect to the other is not perfect, the effective pitch is p2 as shown in FIG. 4B; or p3 as shown in FIG. 4C. Specifically, as shown in FIG. 4B, if the second, unshaded grating shown in FIG. 4B is shifted to the left with respect to the first, shaded grating, the resultant effective grating is p2 which, in the case of the first grating having a pitch of 90 nm, gives a pitch p2 of 90 nm (rather than the smaller 45 nm). Conversely, if the second, unshaded grating of FIG. 4C is shifted to the right slightly with respect to the first, shaded grating, the effective pitch p3 becomes 90 nm as well. This is because the repeated pattern is no longer a single bar, but a double bar with a larger space next to every second bar. Using the method of the state of the art as represented by FIG. 4, the measurement of the change of the effective pitch from p1 to either p2 or p3 demonstrates that there is an overlay error. By determining the scatter spectrum from either of the targets of FIG. 4B or 4C, the size of the overlay error may also be distinguished using known scatterometric methods.

However, what cannot be distinguished from the example shown in FIG. 4 is which way the overlay error is oriented. In other words, the sign (+ or −) of the overlay error remains unmeasurable.

Furthermore, if the pitch resulting from double patterning as shown in FIG. 4 is too dense, then first diffraction orders may not be detected because only the zeroth order will be detectable as a result of the pitch being smaller than the wavelength of the measurement radiation beam. This may result in the overlay not being measurable at all. As the purpose of double patterning is to print very dense lines, a lack of an effective measurement of overlay is a very real problem in the state of the art.

Other examples in the state of the art that attempt to allow denser target gratings while still enabling the measurement of overlay are found in U.S. Pat. No. 7,061,615 B1 (Lowe-Webb), U.S. Pat. No. 6,819,426 B2 (Sezginer et al.) and US 2004/0109165 A1 (Say et al.). These documents describe arrangements of various types of asymmetrical targets, in particular ones where the upper and lower gratings (i.e. a single grating on each subsequent product layer) of an overlay target have different pitches, phases or line widths. There is also the disclosure of an arrangement where misalignment of overlying gratings creates double-pitched gratings. The way that these work is that by knowing the expected spectrum of the top layer and the expected spectrum of the bottom layer (which is different from that of the top layer), the combined spectrum gives the relative positions of the two layers, and thus an overlay error measurement.

It is desirable, for example, to provide a scatterometry target and a method of making the target that enables the size of the grating of the target to be reduced, but without the loss of higher diffraction orders when the pitch of the grating is smaller than the wavelength of the measurement radiation beam.

According to an aspect of the present invention, there is provided substrate having an overlay target comprising a periodic array of structures, wherein every $n^{th}$ structure is different from the rest of the structures, where n is at least 2. The periodic array desirably comprises at least two interlaced gratings and wherein every $m^{th}$ structure of at least one of the gratings is different from the rest of the structures, where m is at least 1.

According to an aspect of the invention, there is provided a method for creating an overlay target on a substrate, comprising forming, on the substrate, a periodic array of structures, wherein every $n^{th}$ structure is different from the rest of the structures, where n is at least 2.

According to an aspect of the present invention, there is provided an inspection method for inspecting overlay error of at least two product layers on a substrate, comprising:
 providing a periodic array of structures on a substrate, wherein every $n^{th}$ structure is different from the rest of the structures and n is at least 2;
 providing a second, identical periodic array of structures on a subsequent product layer on the substrate;
 illuminating the arrays with a radiation beam;
 detecting the radiation beam redirected by the arrays; and
 determining, from one or more properties of the redirected beam, whether the arrays are in alignment with each other.

The determining whether the arrays are in alignment with each other may comprise:
 flipping the image of a detected redirected radiation beam through an axis;
 subtracting the image of the detected redirected radiation beam from the flipped image to obtain an image of the differences between the two images;
 determining, from the image of the differences, the extent and position of the asymmetry of the image of the detected redirected radiation beam; and
 determining the extent and the direction of an overlay error from the extent and position of the asymmetry.

Flipping the image of a detected reflected radiation beam may be through the horizontal axis where vertical gratings are used. For horizontal gratings, the diffraction orders are in the Y-direction, and hence the "flipping" needs to be adjusted accordingly.

According to an aspect of the invention, there are provided an inspection apparatus for inspecting overlay error of at least two product layers on a substrate, a lithographic apparatus and a lithographic cell, each comprising:
 a printing apparatus configured to print an overlay target onto a substrate, the overlay target comprising a periodic array of structures, wherein every $n^{th}$ structure is different from the rest of the structures and n is at least 2, the printing apparatus configured to print the same overlay target onto a subsequent layer of the substrate;
 a detector configured to detect radiation redirected from the overlay targets; and
 a processor configured to determine whether there is an overlay error from the detected redirected radiation.

BRIEF DESCRIPTION OF THE DRAWINGS

Embodiments of the invention will now be described, by way of example only, with reference to the accompanying schematic drawings in which corresponding reference symbols indicate corresponding parts, and in which:

FIGS. 4a, 4b and 4c depict double patterning of a target according to the state of the art;
FIGS. 9a and 9b depict a biased target according to an embodiment of the present invention.

DETAILED DESCRIPTION

Figure 1A:
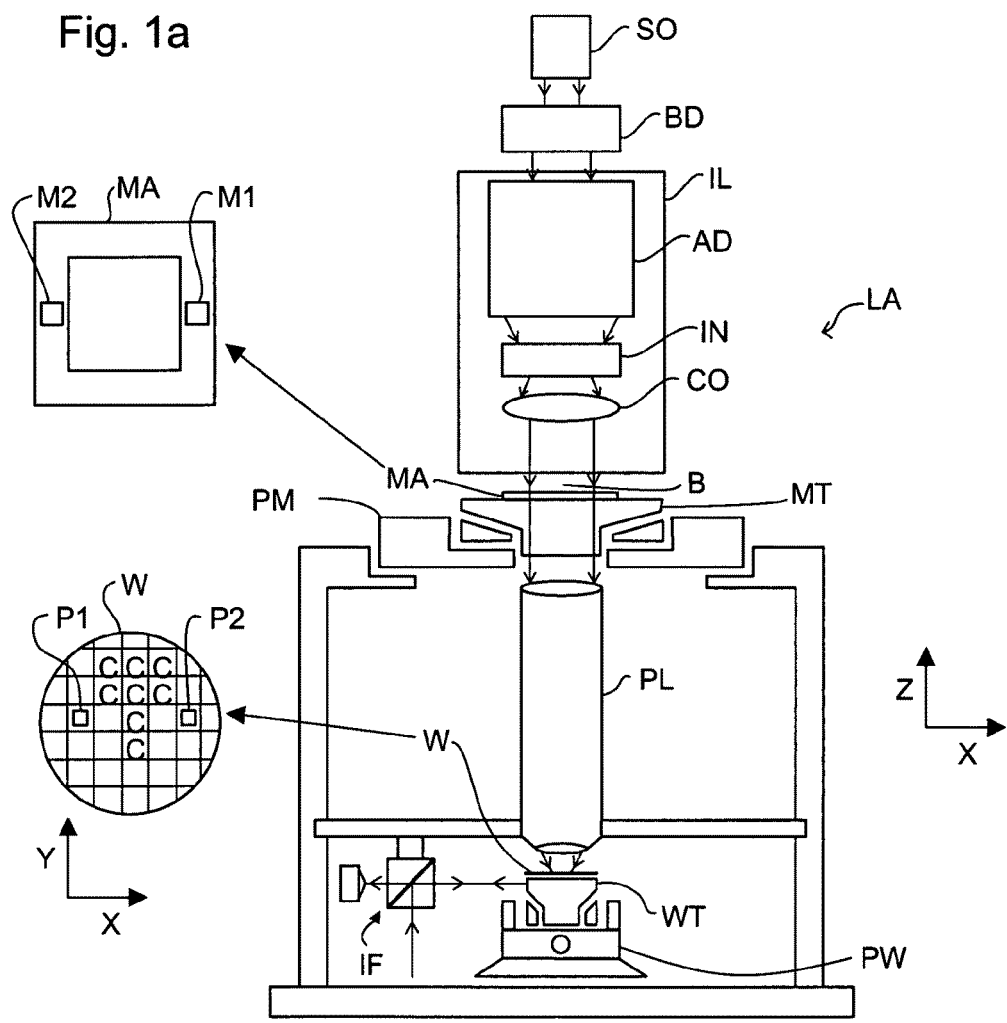
FIG. 1a depicts a lithographic apparatus.

FIG. 1a schematically depicts a lithographic apparatus. The apparatus comprises:
 an illumination system (illuminator) IL configured to condition a radiation beam B (e.g. UV radiation or DUV radiation).
 a support structure (e.g. a mask table) MT constructed to support a patterning device (e.g. a mask) MA and connected to a first positioner PM configured to accurately position the patterning device in accordance with certain parameters;

a substrate table (e.g. a wafer table) WT constructed to hold a substrate (e.g. a resist-coated wafer) W and connected to a second positioner PW configured to accurately position the substrate in accordance with certain parameters; and a projection system (e.g. a refractive projection lens system) PL configured to project a pattern imparted to the radiation beam B by patterning device MA onto a target portion C (e.g. comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure MT holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more substrate tables (and/or two or more patterning device support structures). In such "multiple stage" machines the additional tables/support structures may be used in parallel, or preparatory steps may be carried out on one or more tables/support structures while one or more other tables/support structures are being used for exposure.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1a, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator EL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask) MA, which is held on the support structure (e.g., mask table) MT, and is patterned by the patterning device. Having traversed the patterning device MA, the radiation beam B passes through the projection system PL, which focuses the beam onto a target portion C of the substrate W. With the aid of the second positioner PW and position sensor IF (e.g. an interferometric device, linear encoder, 2-D encoder or capacitive sensor), the substrate table WT can be moved accurately, e.g. so as to position different target portions C in the path of the radiation beam B. Similarly, the first positioner PM and another position sensor (which is not explicitly depicted in FIG. 1a) can be used to accurately position the patterning device MA with respect to the path of the radiation beam B, e.g. after mechanical retrieval from a mask library, or during a scan. In general, movement of the support structure MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the support structure MT may be connected to a short-stroke actuator only, or may be fixed. Patterning device MA and substrate W may be aligned using patterning device alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device MA, the patterning device alignment marks may be located between the dies.

The depicted apparatus could be used in at least one of the following modes:

1. In step mode, the support structure MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the support structure MT and the substrate table WT are scanned synchronously while a pattern imparted to the radiation beam is projected onto a target portion C (i.e. a single dynamic exposure). The velocity and direction of the substrate table WT relative to the support structure MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the support structure MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 1B:
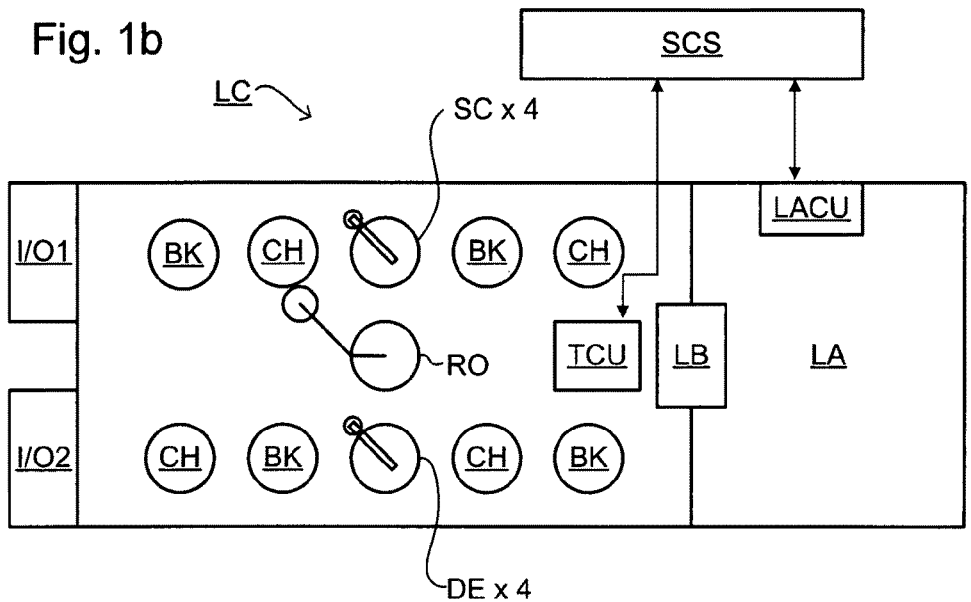
FIG. 1b depicts a lithographic cell or cluster.

As shown in FIG. 1b, the lithographic apparatus LA forms part of a lithographic cell LC, also sometimes referred to as a lithocell or lithocluster, which also includes apparatus to perform one or more pre- and post-exposure processes on a substrate. Conventionally these include one or more spin coaters SC to deposit a resist layer, one or more developers DE to develop exposed resist, one or more chill plates CH and one or more bake plates BK. A substrate handler, or robot, RO picks up a substrate from input/output ports I/O1, I/O2, moves it between the different process devices and delivers it to the loading bay LB of the lithographic apparatus. These devices, which are often collectively referred to as the track, are under the control of a track control unit TCU which is itself controlled by the supervisory control system SCS, which also controls the lithographic apparatus via lithographic control unit LACU. Thus, the different apparatus may be operated to maximize throughput and processing efficiency.

In order that the substrate that is exposed by the lithographic apparatus is exposed correctly and consistently, it is desirable to inspect an exposed substrate to measure one or more properties such as overlay error between subsequent layers, line thickness, critical dimension (CD), etc. If an error is detected, an adjustment may be made to an exposure of one or more subsequent substrates, especially if the inspection can be done soon and fast enough that another substrate of the same batch is still to be exposed. Also, an already exposed substrate may be stripped and reworked (to improve yield) or discarded, thereby avoiding performing an exposure on a substrate that is known to be faulty. In a case where only some target portions of a substrate are faulty, a further exposure may be performed only on those target portions which are good. Another possibility is to adapt a setting of a subsequent process step to compensate for the error, e.g. the time of a trim etch step can be adjusted to compensate for substrate-to-substrate CD variation resulting from the lithographic process step.

An inspection apparatus is used to determine one or more properties of a substrate, and in particular, how one or more properties of different substrates or different layers of the same substrate vary from layer to layer and/or across a substrate. The inspection apparatus may be integrated into the lithographic apparatus LA or the lithocell LC or may be a stand-alone device. To enable most rapid measurements, it is desirable that the inspection apparatus measure one or more properties in the exposed resist layer immediately after the exposure. However, the latent image in the resist has a very low contrast—there is only a very small difference in refractive index between the part of the resist which has been exposed to radiation and that which has not—and not all inspection apparatus have sufficient sensitivity to make useful measurements of the latent image. Therefore measurements may be taken after the post-exposure bake step (PEB) which is customarily the first step carried out on an exposed substrate and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibility for rework of a faulty substrate but may still provide useful information, e.g. for the purpose of process control.

Figure 2:
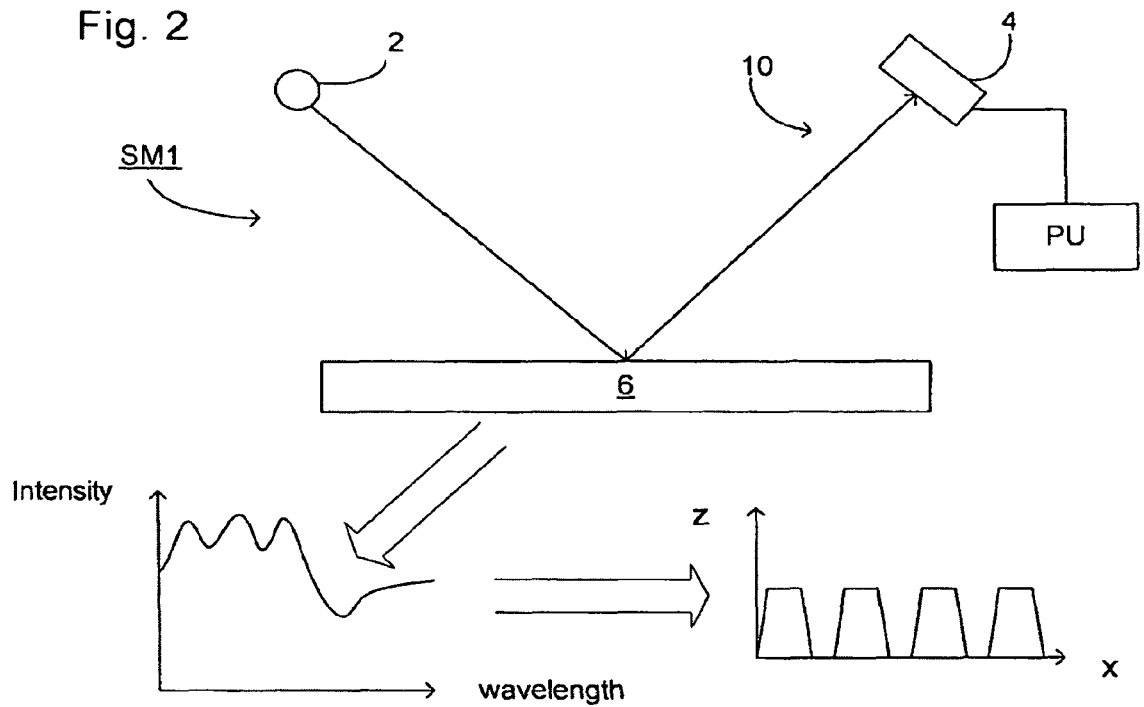
FIG. 2 depicts a first scatterometer.

FIG. 2 depicts a scatterometer SM1 according to an embodiment of the invention. It comprises a broadband (white light) radiation projector 2 which projects radiation onto a substrate 6. The reflected radiation is passed to a spectrometer detector 4, which measures a spectrum 10 (i.e. a measurement of intensity as a function of wavelength) of the specular reflected radiation. From this data, the structure or profile giving rise to the detected spectrum may be reconstructed by processing unit PU, e.g. by Rigorous Coupled Wave Analysis and non-linear regression or by comparison with a library of simulated spectra as shown at the bottom of FIG. 2. In general, for the reconstruction, the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Figure 3:
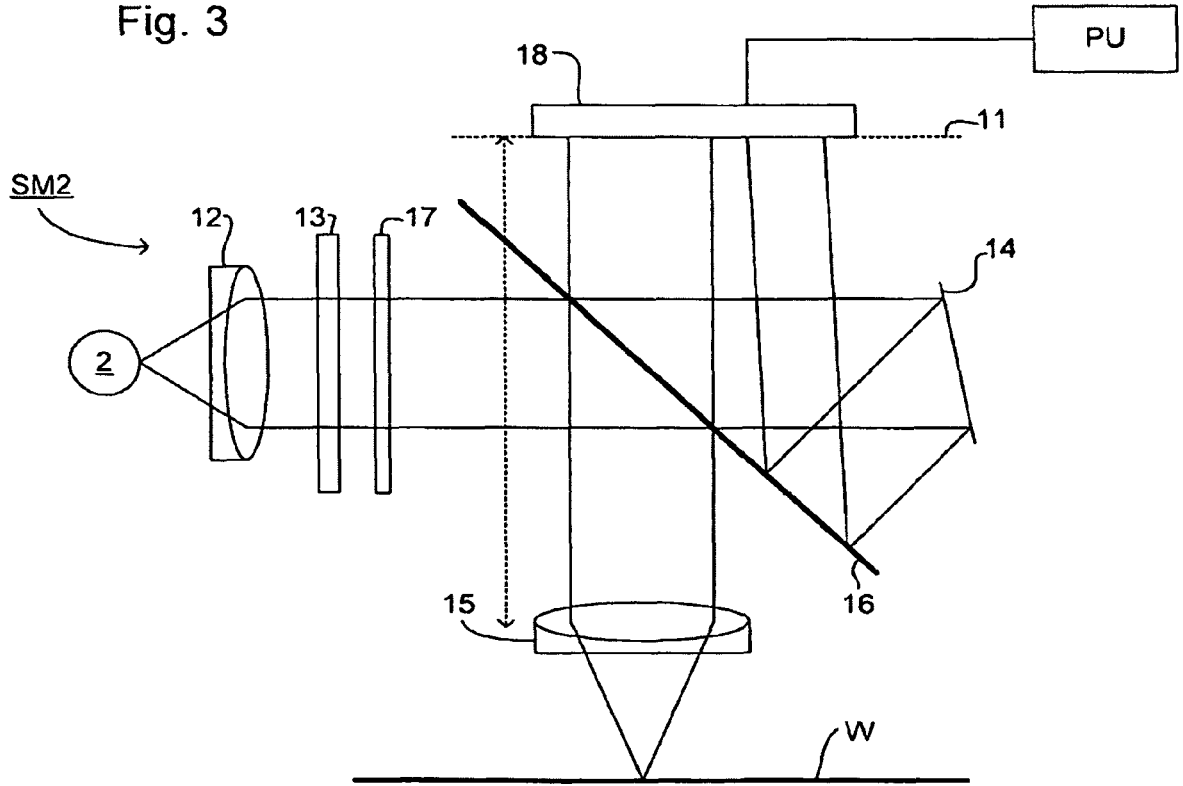
FIG. 3 depicts a second scatterometer.

Another scatterometer SM2 according to an embodiment of the invention is shown in FIG. 3. In this device, the radiation emitted by radiation source 2 is focused using lens system 12 through interference filter 13 and polarizer 17, reflected by partially reflective surface 16 and is focused onto substrate W via a microscope objective lens 15, which has a high numerical aperture (NA), desirably at least 0.9 or at least 0.95. An immersion scatterometer may even have a lens with a numerical aperture over 1. The reflected radiation then transmits through partially reflective surface 16 into a detector 18 in order to have the scatter spectrum detected. The detector may be located in the back-projected pupil plane 11, which is at the focal length of the lens 15, however the pupil plane may instead be re-imaged with auxiliary optics (not shown) onto the detector 18. The pupil plane is the plane in which the radial position of radiation defines the angle of incidence and the angular position defines the azimuth angle of the radiation. The detector is desirably a two-dimensional detector so that a two-dimensional angular scatter spectrum (i.e. a measurement of intensity as a function of angle of scatter) of the substrate target can be measured. The detector 18 may be, for example, an array of CCD or CMOS sensors, and may have an integration time of, for example, 40 milliseconds per frame.

A reference beam is often used, for example, to measure the intensity of the incident radiation. To do this, when the radiation beam is incident on the partially reflective surface 16 part of it is transmitted through the surface as a reference beam towards a reference mirror 14. The reference beam is then projected onto a different part of the same detector 18.

One or more interference filters 13 are available to select a wavelength of interest in the range of, say, 405-790 nm or even lower, such as 200-300 nm. The interference filter(s) may be tunable rather than comprising a set of different filters. A grating could be used instead of or in addition to one or more interference filters.

The detector 18 may measure the intensity of scattered radiation at a single wavelength (or narrow wavelength range), the intensity separately at multiple wavelengths or the intensity integrated over a wavelength range. Further, the detector may separately measure the intensity of transverse magnetic-(TM) and transverse electric-(TE) polarized radiation and/or the phase difference between the transverse magnetic- and transverse electric-polarized radiation.

Using a broadband radiation source 2 (i.e. one with a wide range of radiation frequencies or wavelengths—and therefore of colors) is possible, which gives a large etendue, allowing the mixing of multiple wavelengths. The plurality of wavelengths in the broadband desirably each has a bandwidth of $\delta\lambda$ and a spacing of at least $2\delta\lambda$ (i.e. twice the wavelength bandwidth). Several "sources" of radiation may be different portions of an extended radiation source which have been split using, e.g., fiber bundles. In this way, angle resolved scatter spectra may be measured at multiple wavelengths in parallel. A 3-D spectrum (wavelength and two different angles) may be measured, which contains more information than a 2-D spectrum. This allows more information to be measured which increases metrology process robustness. This is described in more detail in U.S. patent application publication no. US 2006-0066855, which document is hereby incorporated in its entirety by reference.

In any of the scatterometers described above, the target on substrate W may be a grating which is printed such that after development, the bars are formed of solid resist lines. The bars may alternatively be etched into the substrate. The target pattern is chosen to be sensitive to a parameter of interest, such as focus, dose, overlay, chromatic aberration in the lithographic projection apparatus, etc., such that variation in the relevant parameter will manifest as variation in the printed target. For example, the target pattern may be sensitive to chromatic aberration in the lithographic projection apparatus, particularly the projection system PL, and illumination symmetry and the presence of such aberration will manifest itself in a variation in the printed target pattern. Accordingly, the scatterometry data of the printed target pattern is used to reconstruct the target pattern. The parameters of the target pattern, such as line width and shape, may be input to the reconstruction process, performed by a processing unit PU, from knowledge of the printing step and/or other scatterometry processes.

An embodiment of the invention is concerned with the printing of a target for the measurement of one or more parameters, for example, the critical dimension (CD) and overlay, of a printed pattern. In order to overcome the concern of minimizing scribe lane space that is used by measurement targets while allowing meaningful measurements to be obtained, an embodiment of the invention uses a "double patterning" technique. The double patterning technique involves printing two separate patterns (e.g., gratings) either on top of each other or on the same layer such that one pattern is interlaced with the other, giving rise to a single, denser pattern with an effective pitch determined by the interaction of the two separate patterns. What one or more embodiments of the patterning technique disclosed herein have in common is that every $n^{th}$ feature (e.g., line) in a pattern (e.g., a grating) of small pitch is different from every other feature. This difference of the $n^{th}$ (e.g. second or third) feature (e.g., line or bar or structure) may be in its width, height, or simply in its omission. The resultant pattern will then have two pitches, one of which is comparable to the wavelength of the measurement radiation beam and hence able to produce diffraction orders that may be captured in the pupil plane of the scatterometer and therefore be captured by the detector.

Figure 5:
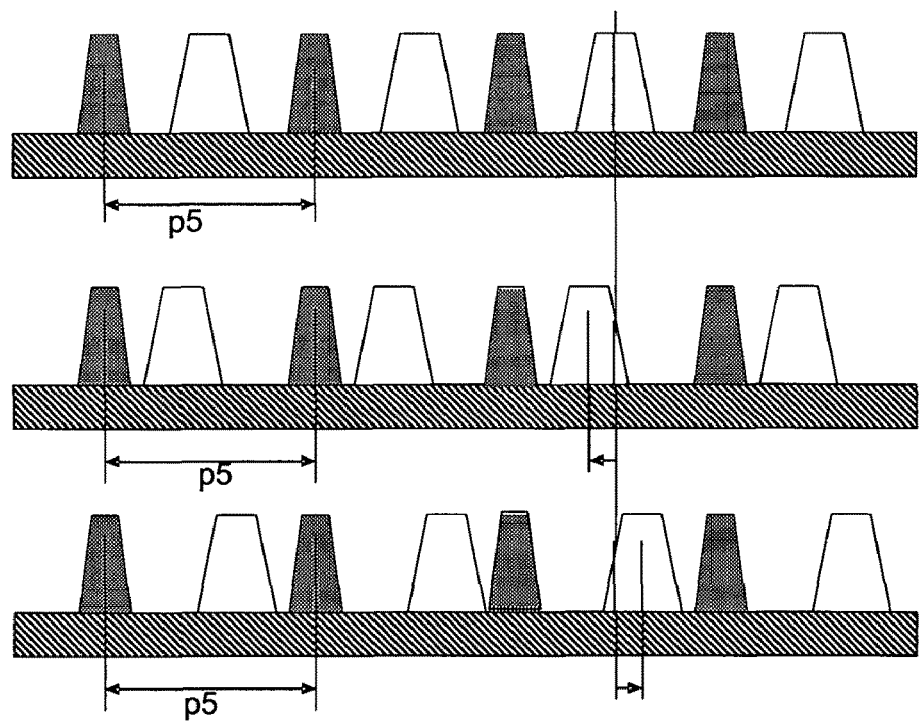
FIG. 5 depicts normal and biased targets according to an embodiment of the present invention.

An embodiment using a grating is shown in FIG. 5. The grating as shown in the top layer of FIG. 5 comprises alternating thin and thick bars. In other words, a first (e.g. shaded) grating is created with bars having a first line width and a second (e.g. unshaded) grating is superimposed that comprises bars with a second (in this case, larger) line width. The difference in line width will cause an asymmetry in the measurement signal that can be detected, as will be discussed with respect to FIGS. 8 to 11 later.

The two superimposed gratings may be created by the use of a mask or during exposure of the substrate. The gratings may thereby be produced at the same time, or one after the other. Yet alternatively, the gratings may be produced even on different product layers. The gratings may be created in any order and with any separation of product layers, by any means, as long as the result is that the (at least) two gratings are positioned in an interlaced position such that the effective pitch may be different from the pitch from one bar to the next, and thereby may remain constant, even with an offset of one of the gratings. When the pitch is constant (and larger than the wavelength of the measurement beam), overlay error may more efficiently be measured.

Specifically, an advantage afforded by this embodiment is that there is no change in pitch p5 if one grating is shifted to the left, as shown in the middle layer of FIG. 5, or to the right, as shown in the bottom layer of FIG. 5, with respect to the other grating. In other words, there is no moiré or aliasing effect.

The reason that having a constant pitch is advantageous is that an asymmetry in the target may be created by shifting one of the gratings (e.g. the unshaded, wider-line width grating) by a small amount in one or other direction with respect to the other grating. The benefit of this is that overlay of two exposures in one or more layers may then be measured and any misalignment of subsequent layers determined such that corrections may be made to the exposure step to correct for any overlay error. As mentioned earlier, if the two superimposed gratings of a measurement target are identical, and a subsequent layer is placed over the top of this layer with an identical measurement target, but that is shifted slightly with respect to the bottom layer, an overlay error will be noticed, but the direction of the error may not be noticed because an overlay error of half a pitch in a positive direction will look the same as an overlay error of half a pitch in the negative (i.e. opposite) direction. If the measurement targets are asymmetric (as they are shown in FIG. 5, for example), they cause an asymmetry in their resultant spectra and an overlay error in one direction will give rise to a different spectrum from an overlay error in the opposite direction.

The embodiment as shown in FIG. 5 is successful if the pitch of the first grating is greater than about ⅔ of the wavelength of the radiation beam that will irradiate it. However, when the pitch becomes too dense to be detected easily (i.e. the pitch is smaller than about ⅔ of the wavelength of the measurement radiation beam and first or higher diffraction orders are no longer present in the pupil plane of the detector), the pitch may be artificially increased as shown in FIG. 6.

Figure 6:
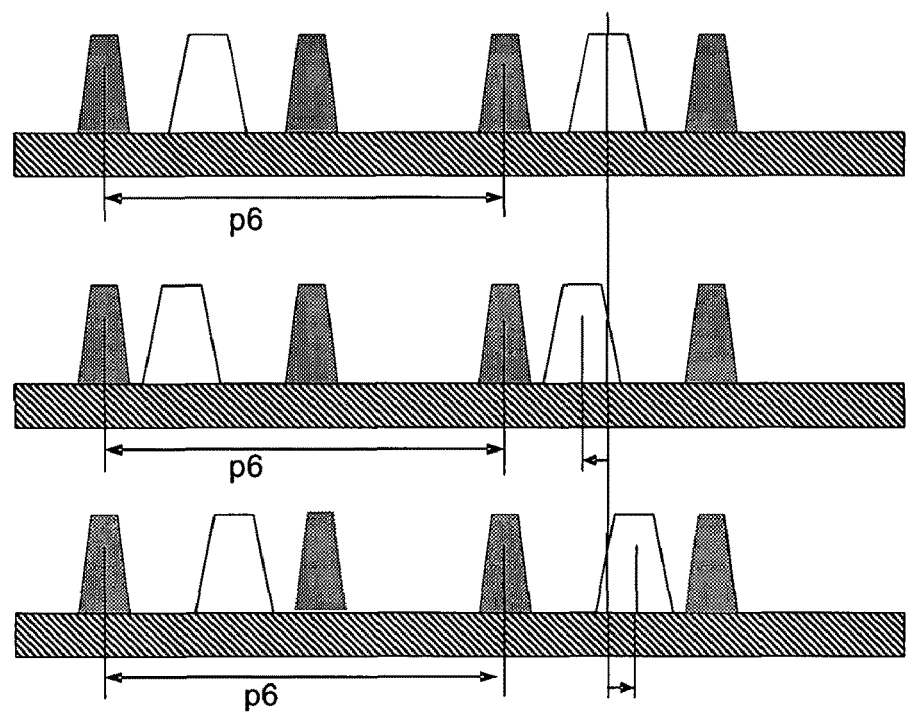
FIG. 6 depicts biased targets and pitch doubling according to an embodiment of the present invention.

FIG. 6 shows an artificially increased pitch p6 that is taken to be twice the pitch of the first grating shown as shaded lines. This is possible by making the pitch of the second, unshaded, grating twice the pitch of the first grating that is shaded. As shown in the second and third lines of FIG. 6, the pitch p6 will not alter even if the second, unshaded grating is shifted to the left or to the right respectively.

The effective pitch is increased by the relationship between the superimposed gratings. As can be seen in FIG. 6, the first, shaded grating is the same as in FIG. 4 or 5. However, the second, wider, unshaded grating is only present between alternate bars of the first, shaded grating. The pitch of the second, unshaded grating is therefore twice the pitch of the first, shaded grating. The resultant pitch p6 is the distance within which the pattern of the target is repeated, which is at twice the pitch of the first, shaded grating. Moreover, there is no change in pitch p6 if the second, unshaded grating is shifted to the left with respect to the first, shaded grating, as shown in the middle layer of FIG. 6, or to the right, as shown in the bottom layer of FIG. 6. The pitch remains the same because the repeated pattern covers the same distance.

Like the embodiment of FIG. 5, constant pitch is not the only benefit of this sort of target. A further or alternative benefit comes from the asymmetry of the target that allows overlay error in any direction to be accurately determined. The asymmetry is used not only to determine in which direction the overlay error is biased, but also to determine the extent of the overlay error by virtue of the extent of variation in asymmetry that spectra resulting from measurement beams reflecting from the targets will experience. The asymmetry acts as a sort of flag for indicating that an overlay error exists, and then the particular parameters of the resultant spectra will indicate the extent and direction of the overlay error.

Figure 7:
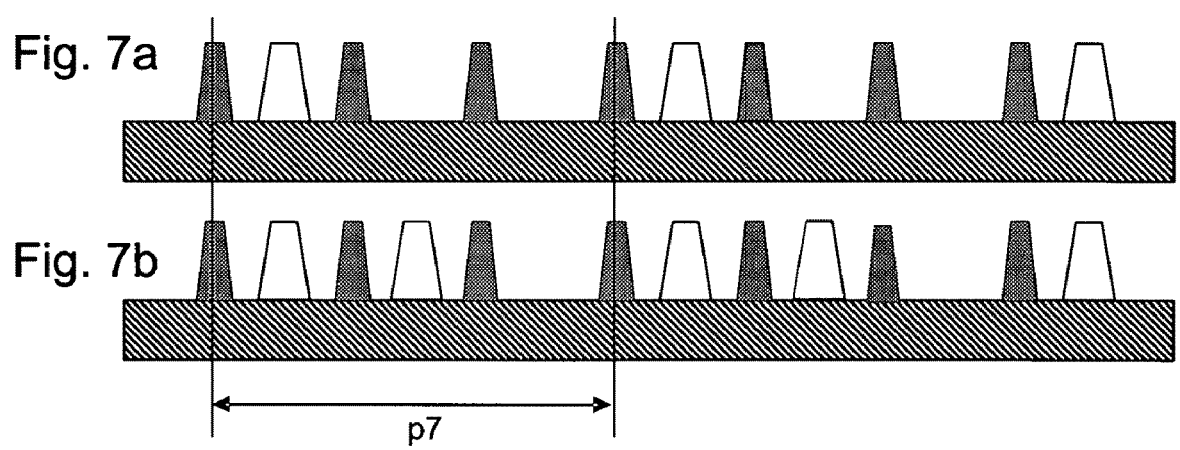
FIG. 7 depicts biased targets and pitch tripling according to an embodiment of the present invention.

If the pitch as shown in FIG. 6 is still too dense to be easily detected, an even larger pitch may be created. Using a similar method to the pitch doubling method as shown in FIG. 6, pitch tripling may be accomplished as shown in FIG. 7.

Pitch tripling may be carried out in several ways. Two ways are shown in FIGS. 7A and 7B. FIG. 7A shows a first grating of regular pitch as an array of shaded bars. This is, in fact, the same first, shaded grating as shown in FIGS. 4 to 6. A second, unshaded grating with a pitch that is three times that of the first, shaded grating is superimposed onto the first, shaded grating. The effective pitch p7 is now three times the pitch of the first shaded grating. As can be seen in FIG. 7A, the repetition of the pattern occurs every three times the pitch of the first grating (i.e. it is set by the pitch of the larger-pitched grating).

Alternatively, as shown in FIG. 7B, the first, shaded grating is the same as the embodiment of FIG. 7A but the second, unshaded grating is superimposed such that an unshaded bar is present between two adjacent pairs of shaded bars, then it is omitted between the third pair before starting the pattern again. Again, the effective pitch p7 is three times the pitch of the first, shaded grating because it is dictated by the larger pitch of the second, unshaded grating.

In this way, the effective pitch can be increased such that the first diffraction order (at least) appears in the pupil plane image. The result of this is that an asymmetry signal is boosted, making detection of parameters such as overlay error and CD much easier.

Figure 8B:
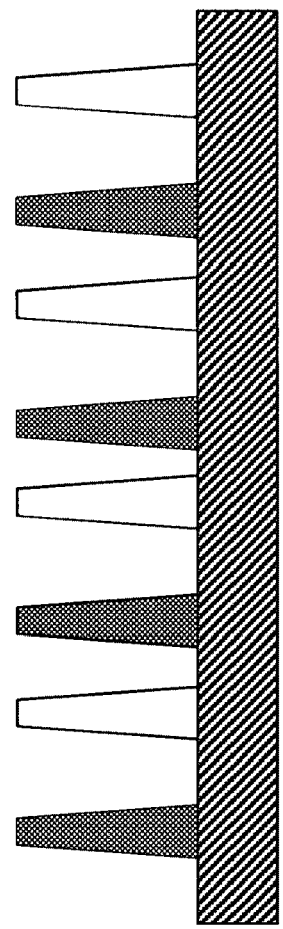
FIGS. 8a and 8b depict an unbiased target.
Figure 8A:
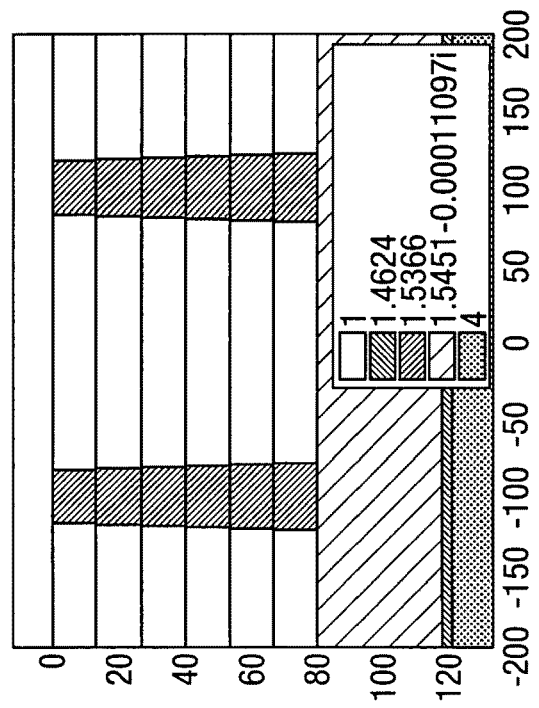
Figure 8D:
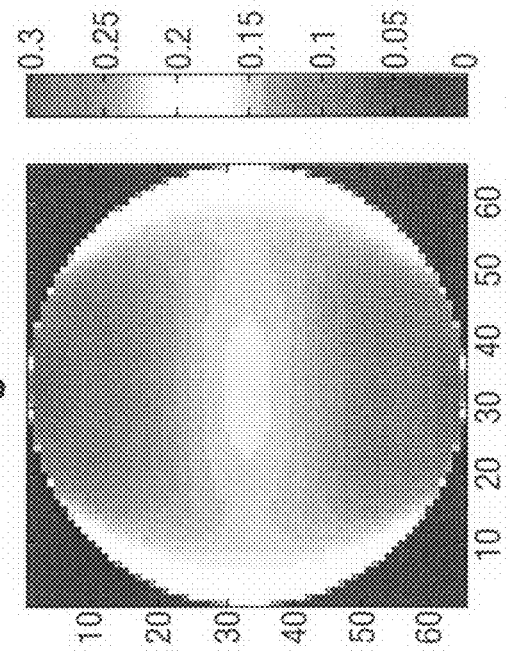
FIGS. 8c, 8d, 8e and 8f depict the transverse electric (TE) and transverse magnetic (TM) images of the target of FIGS. 8a and 8b.
Figure 8F:
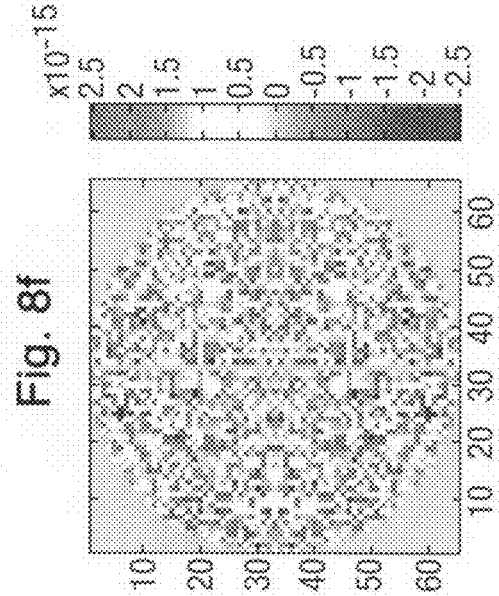
Figure 8C:
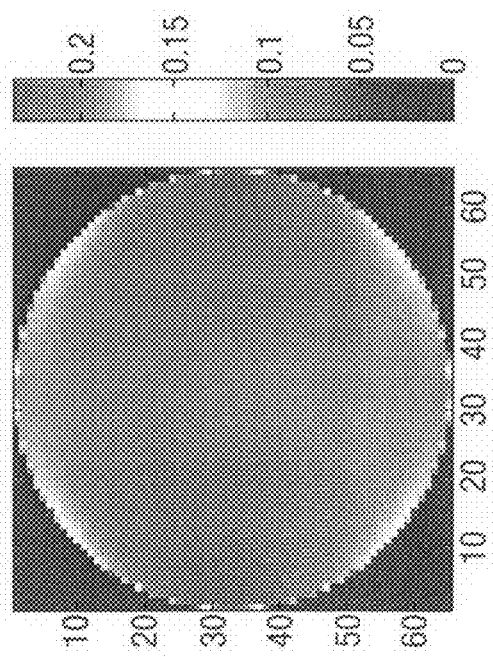

FIG. 8a depicts two bars of a 2-D grating target, wherein each refractive index is shown in a different shade. The atmosphere surrounding the two bars has a refractive index of 1. The bars of the grating have a refractive index of 1.5366, the substrate layer supporting the grating has a refractive index of 1.5451-0.00011097i, the layer below the substrate layer has a refractive index of 1.4624 and the bottom layer has a refractive index of 4. FIG. 8b shows the grating of FIG. 8a with a second grating depicted as an unshaded grating alternately superimposed (or "interlaced"). The grating is unbiased (i.e. symmetrical) but has an overlay error of 10 nm. FIG. 8c shows the transverse electric (TE) image using an angle resolved scatterometer. FIG. 8d shows the transverse magnetic (TM) image as measured using an angle resolved scatterometer.

Figure 8E:
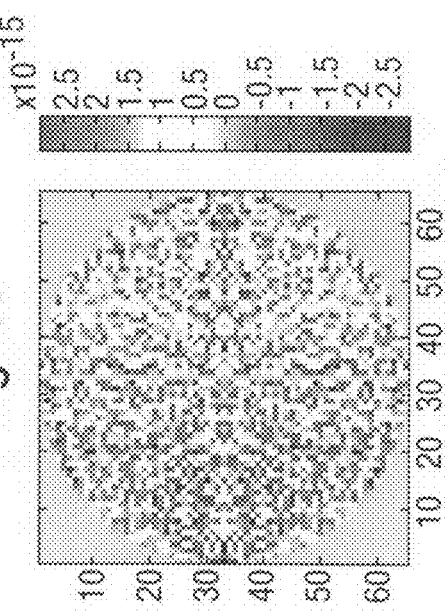

If an asymmetry is present, it is a difference between the upper and lower portions of the TE or TM image, though difficult to distinguish from these images alone. The asymmetry of the gratings is therefore calculated by subtracting the horizontally flipped image from the original image (if the imaged gratings are vertical, the symmetry would be interesting in the horizontal direction). FIGS. 8e and 8f respectively show the asymmetry in the TE and TM images of FIGS. 8c and 8d, respectively. Alternatively, the flipping may be carried out in the vertical axis where horizontal gratings are being used.

With no bias in the gratings but with an overlay error, very little asymmetry is visible in the asymmetry images.

Figure 9D:
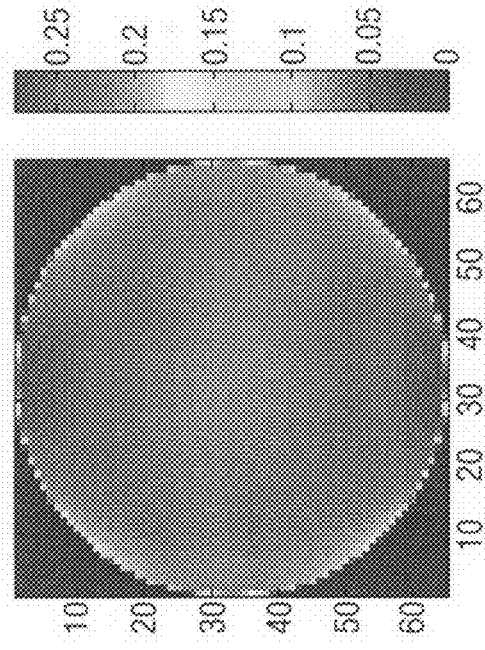
FIGS. 9c, 9d, 9e and 9f depict the transverse electric (TE) and transverse magnetic (TM) images of the target of FIGS. 9a and 9b.

Conversely, referring to FIG. 9, FIG. 9a depicts one bar each of two gratings, the refractive indices being the same as for FIG. 8a. FIG. 9b shows the relationship between the first, shaded grating (the left bar in FIG. 9a) and the second, unshaded grating (the right bar in FIG. 9a). Here, there is a bias of 20 nm but only a 1 nm overlay error. FIG. 9c shows the TE image using an angle resolved scatterometer and FIG. 9d shows the TM image using an angle resolved scatterometer. FIGS. 9e and 9f respectively show the asymmetry of the TE image of FIG. 9c and the TM image of FIG. 9d, respectively. As can be seen from the dark patches in FIGS. 9e and 9f, an asymmetry in both the TE and TM images is evident. Even a small overlay error of just 1 nm results in a clear asymmetry signal. The dark patches therefore indicate that there is an overlay error. The position and density of the patches will indicate how large the overlay error is and in which direction the error is biased.

Figure 10A:
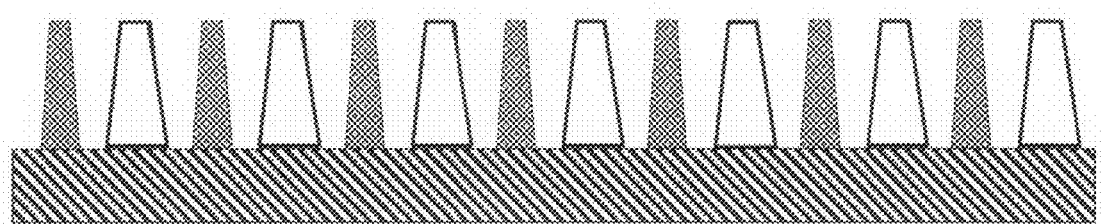
FIGS. 10a, 10b and 10c depict double patterning, where one of the lines is given a bias.
Figure 10B:
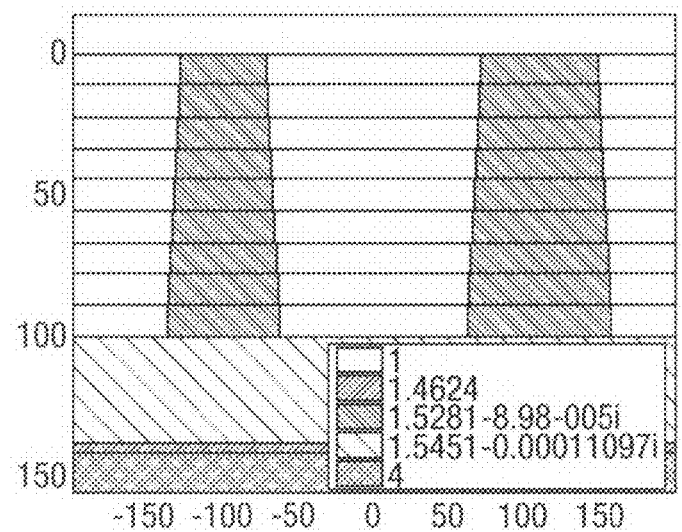
Figure 10C:
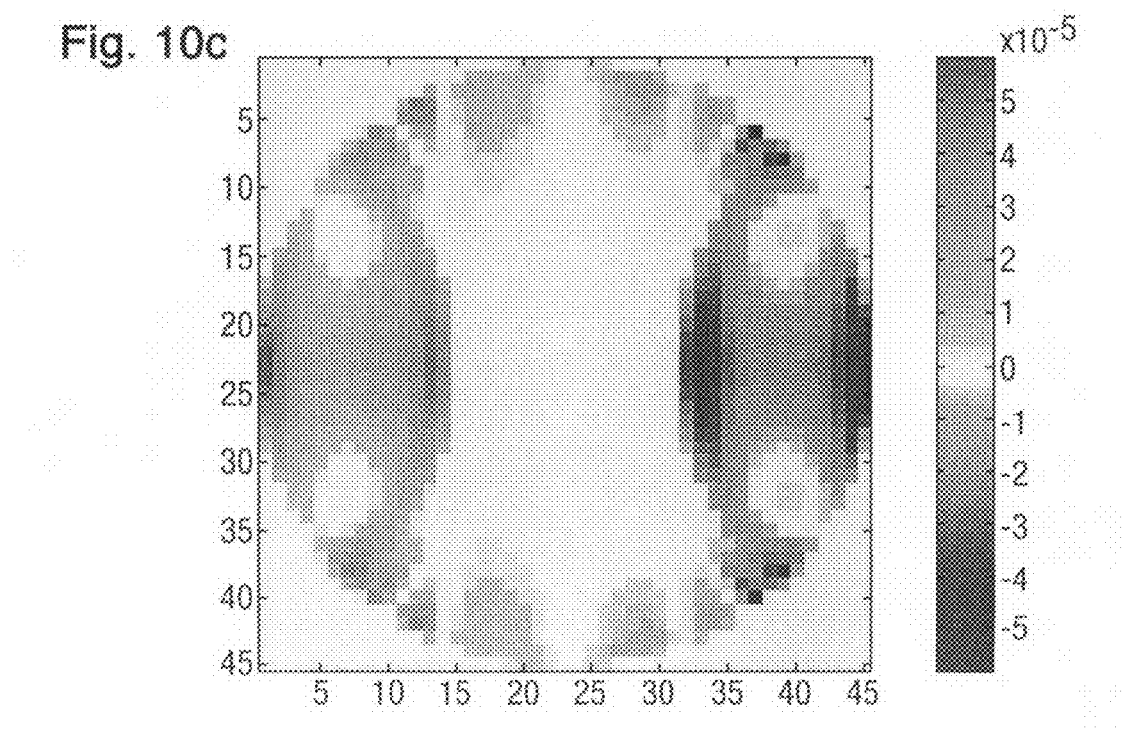

In the measurements depicted and described above, measurement noise is not accounted for. When this is the case, even the smallest overlay error is detected. If, however, some measurement noise is present, subtle differences in symmetry may be difficult to measure because the noise may appear as dark patches or differences in the top and bottom portions of the TE or TM images and thereby appear as asymmetries. In this case, the signal can be boosted by artificial pitch doubling or even tripling as described with reference to FIGS. 6 and 7. FIGS. 10 and 11 demonstrate a comparison of the asymmetry measurements between a single pitch pattern and a double pitch pattern. Double patterning (i.e. the use of two superimposed gratings) is used in both cases. FIG. 10a depicts a first, shaded grating with a first line width and a superimposed, second, unshaded grating that has a greater line width and is therefore referred to as having a bias. FIG. 10b shows the respective size of the bars of the two gratings (a bar of the first, shaded grating is shown on the left and a bar of the second, unshaded grating is shown on the right) and the refractive indices of the respective portions of the substrate, bars and atmosphere as described earlier. FIG. 10c shows the asymmetry of a diffracted image of the grating of FIG. 10a.

Figure 11A:
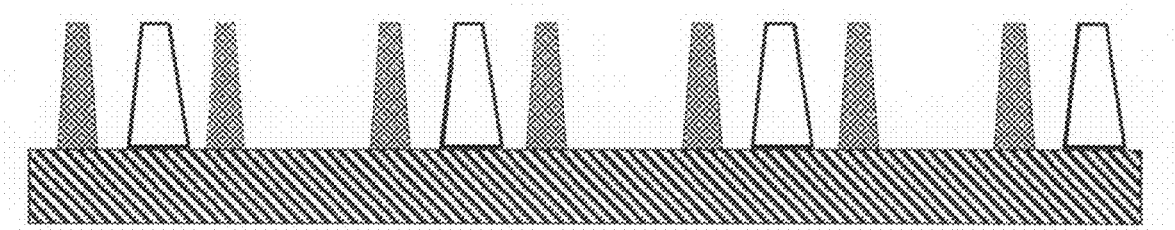
FIGS. 11a, 11b and 11c depict double patterning according to an embodiment of the invention, where one of the patterns is given an offset and the pitch is doubled.
Figure 11B:
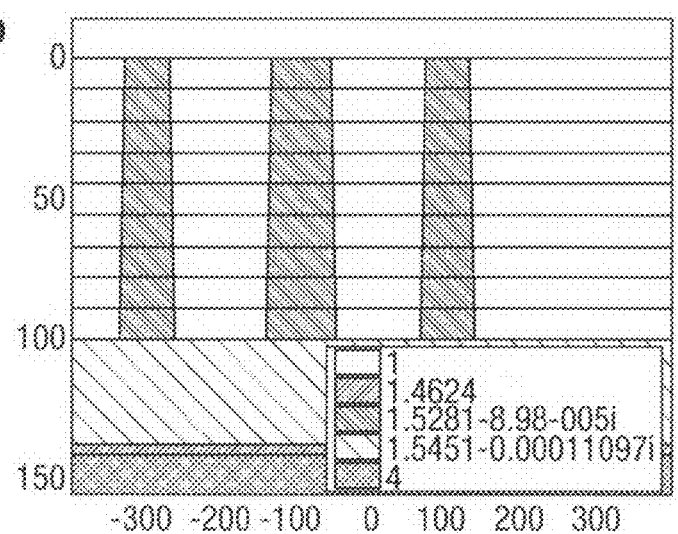
Figure 11C:
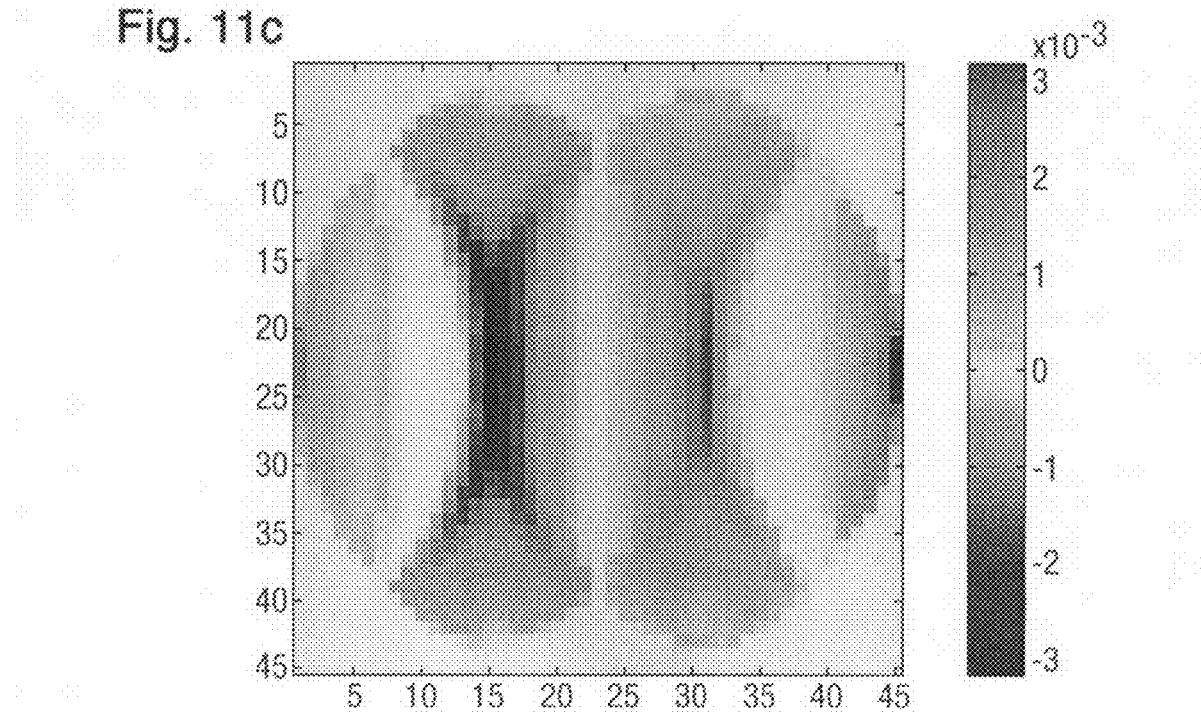

FIG. 11a shows a first, shaded grating with the same pitch as the first grating of FIG. 10a. A second, unshaded grating is superimposed into every alternate space between the bars of the first grating. The second grating also has a greater line width than the first grating. The effective pitch of the gratings of FIG. 11a is therefore twice that of FIG. 10a. FIG. 11b show the respective size of the bars of the two gratings (a bar of the first, shaded grating is shown on the left and on the right and a bar of the second, unshaded grating is shown in the middle) and the refractive indices of the respective portions of the substrate, bars and atmosphere as described earlier. FIG. 11c shows the asymmetry of a diffracted image of a measurement radiation beam that has been diffracted from the gratings of FIG. 11a.

Figure 9F:
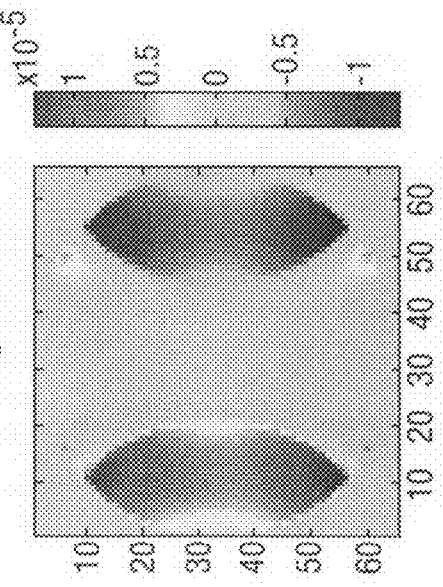
Figure 9C:
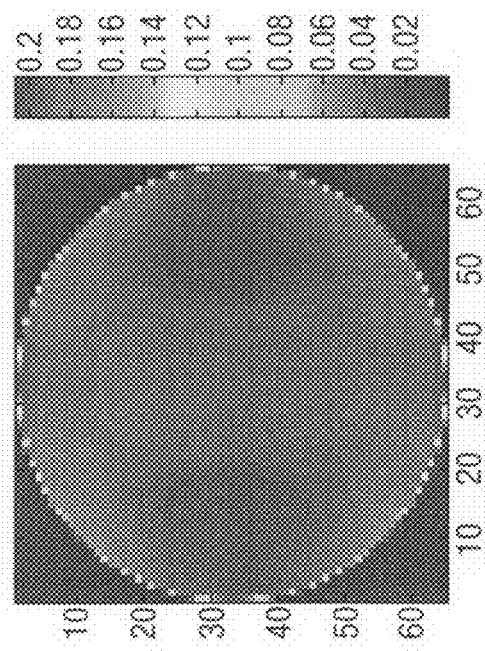
Figure 9E:
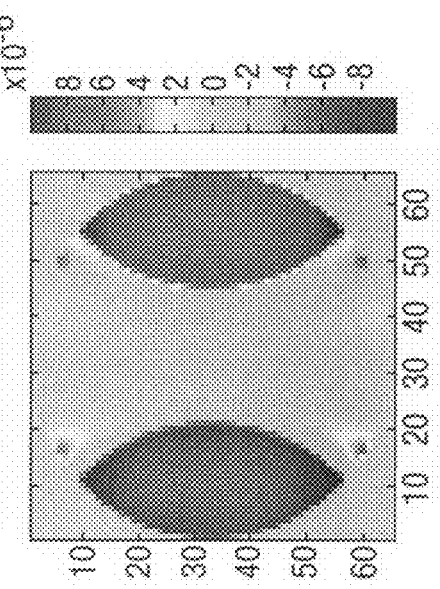

The scale of the asymmetry image of FIG. 10c has a scale to $10^{-5}$ (as an "amount" of asymmetry; i.e. a difference in reflection coefficient. The original image such as that shown in FIG. 9c depicts the reflection coefficient, and the image such as that shown in FIGS. 9e and 9f show the asymmetry in the reflection coefficients. The amount of asymmetry is the difference in reflection coefficient of the left and right side of the pupil image). On the other hand, the asymmetry of the image in FIG. 11c has a scale of $10^{-3}$. The signal is enhanced in the asymmetry image of FIG. 11c by two orders of magnitude with respect to the asymmetry image of FIG. 10c. Where the signal in FIG. 10c may be below the detection, limit of an optical sensor, the image of FIG. 11c should pose no problems.

The above embodiments are just example of the possibilities when every n h feature (in these cases, every $n^{th}$ bar) is different from the rest of the features. Every $n^{th}$ feature may be a different shape or it may be omitted or it may be thicker or thinner or taller or shorter. Any difference will enable the effective pitch to be far greater than the actual pitch of the first grating.

Furthermore, the gratings as shown in a single dimension in the Figures may also be extended in two dimensions. The variance in pitch would therefore apply in both the x and y directions.

Although the embodiments above only describe this asymmetry application to a grating in a single layer, measurements of overlay between different product layers could equally be measured in this way.

Furthermore, by superimposing the different gratings, the previous practice of having two gratings for each direction next to each other, which takes up more space, would no longer be necessary.

The "default" overlay measurement described herein is based on the asymmetry of the grating. Showing the presence of the asymmetry is one thing—and for this purpose the subtraction of the flipped image is very useful—but calculating the actual overlay is a different matter. In the default case, to measure an overlay in the x-direction, two gratings are required. In the currently described method a profile reconstruction may be carried out using, e.g., RCWA. In this model, the relative position of the two pitches are used as a free parameter, and as a result the overlay can be measured.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

The invention claimed is:

1. A method for creating an overlay target on a substrate, comprising:
    forming, on the substrate, a first periodic array of structures with a first pitch;
    forming, on the substrate, a second periodic array of structures with a second pitch, the second array being different than the first array, and the second pitch being different from the first pitch;
    interlacing the first periodic array of structures with the second periodic array of structures; and determining an effective pitch of the interlaced arrays wherein only the first pitch is comparable to a wavelength of a measurement radiation beam.

2. The method of claim 1, wherein the overlay target is etched onto the substrate.

3. The method of claim 1, wherein the overlay target is exposed on the substrate.

4. The method of claim 1, wherein structures in the first periodic array of structures are wider than structures in the second periodic array of structures.

5. The method of claim 1, wherein structures in the first periodic array of structures are narrower than structures in the second periodic array of structures.

6. The method of claim 1, wherein structures in the first periodic array of structures are taller than structure in the second periodic array of structures.

7. The method of claim 1, wherein structures in the first periodic array of structures are shorter than structures in the second periodic array of structures.

8. The method of claim 1, wherein structures in the first periodic array of structures are offset with respect to structure in the second periodic array of structures.

9. The method of claim 1, wherein the interlacing comprises interlacing the first periodic array of structures between every two structures of the second periodic array of structures.

10. The method of claim 1, wherein the interlacing comprises interlacing a structure of the first periodic array of structures between every three structures of the second periodic array of structures.

11. The method of claim 1, wherein every $n^{th}$ structure of the first periodic array of structures is omitted.

12. The method of claim 1, wherein structures in the first periodic array of structures are one-dimensional.

13. The method of claim 1, wherein structures in the first periodic array of structures are two-dimensional.

14. The method of claim 1, wherein the first and second periodic array of structures comprises at least two gratings.

15. The method of claim 1, wherein structures in the first and second periodic array of structures comprise at least two gratings.

16. The method of claim 12, wherein the structures are bars.

17. The method of claim 13, wherein structures in the first periodic array of structures comprises structures in both of the x- and y-axes.

18. The method of claim 14, wherein a first grating of the gratings is printed on the substrate and a second grating of the gratings is printed on a subsequent product layer on the substrate.

19. The method of claim 14, wherein a first grating of the gratings is printed on a first product layer on the substrate and a second grating of the gratings is printed on a subsequent product layer on the substrate.

20. The method of claim 15, wherein every second structure of at least one of the gratings is different from the rest of the structures.

21. The method of claim 15, wherein every third structure of at least one of the gratings is different from the rest of the structures.

22. The method of claim 15, wherein a first grating of the gratings is arranged on a first layer on the substrate and a second grating of the gratings is arranged on a second layer on the substrate.

23. The method of claim 15, wherein the pitch of a first grating of the gratings is smaller than a measurement radiation beam to be reflected or diffracted from the array.

24. The method of claim 15, wherein the pitch of a first grating of the gratings is approximately 200 nm.

25. The method of claim 15, wherein at least one of the gratings is arranged such that the effective pitch of the array is larger than the pitch of the grating with the smallest pitch.

26. The method of claim 25, wherein the effective pitch of the array is greater than a wavelength of a measurement radiation beam to be reflected or diffracted from the array.

27. A method comprising, comprising:
    forming a first periodic array of structures with a first pitch on a first layer of a substrate;
    forming a second periodic array of structures with a second pitch on the first layer of the substrate, the second array being different than the first array, and the second pitch being different than the first pitch;
    interlacing the first periodic array of structures with the second periodic array of structures;
    determining an effective pitch of the interlaced arrays wherein only the first pitch is comparable to a wavelength of a measurement radiation beam;
    forming a third periodic array of structures, substantially identical to the first periodic array of structures, on a second layer of the substrate;
    forming a fourth periodic array of structures, substantially identical to the second periodic array of structures, on the second layer on the substrate;
    illuminating the arrays with the radiation beam;
    detecting the radiation beam redirected by the arrays; and
    determining, from one or more properties of the redirected beam, whether the first and second arrays are in alignment with the third and fourth arrays.

28. The method of claim 27, wherein the first and second periodic arrays comprise two gratings such that the pitch of one of the gratings with a largest pitch determines the effective pitch of the arrays and the radiation beam comprises a wavelength that is greater than the effective pitch of the arrays.

29. The method of claim 27, wherein determining whether the first and second arrays are in alignment with the third and fourth arrays comprises:
    flipping an image of a detected redirected radiation beam through an axis;
    subtracting the image of the detected redirected radiation beam from the flipped image to obtain an image of the differences between the two images;
    determining, from the image of the differences, an extent and position of an asymmetry of the image of the detected redirected radiation beam; and
    determining an extent and direction of an overlay error from the extent and position of the asymmetry.

30. An inspection apparatus, comprising:
    a projection system configured to project a pattern to form an overlay target on a substrate, the overlay target comprising a first periodic array of structures with a first pitch and a second periodic array of structures with a second pitch on the substrate, the first and second periodic arrays having different structures, and wherein the first pitch is different from that of the second pitch,
    wherein the first periodic array of structures is interlaced with the second periodic array of structures,
    wherein an effective pitch of the interlaced arrays is determined wherein only the first pitch is comparable to a wavelength of a measurement radiation beam, and wherein the effective pitch remains constant if the first periodic array of structures is misaligned on the substrate in relationship to the second periodic array of structures;

a detector configured to detect radiation redirected from the overlay target; and a processor configured to determine whether there is an overlay error from the detected redirected radiation.

31. A lithographic apparatus comprising:

a projection system configured to project a pattern to form an overlay target on a substrate, the overlay target comprising a first periodic array of structures with a first pitch and a second periodic array of structures with a second pitch on the substrate, the first and second periodic arrays having different structures, and wherein the first pitch is different from that of the second pitch, wherein the first periodic array of structures is interlaced with the second periodic array of structures, wherein a feature of the first periodic array of structure is different from the same feature of the second array of structures, wherein an effective pitch of the interlaced arrays is determined wherein only the first pitch is comparable to a wavelength of a measurement radiation beam, and wherein the effective pitch remains constant if the first periodic array of structures is misaligned on the substrate in relationship to the second periodic array of structures, the projection system configured to print the same overlay target onto a subsequent layer of the substrate;

a detector configured to detect radiation redirected from the overlay targets; and a processor configured to determine whether there is an overlay error from the detected redirected radiation.

32. A lithographic cell comprising:

a projection system configured to project a pattern to form an overlay target on a substrate, the overlay target comprising a first periodic array of structures with a first pitch and a second periodic array of structures with a second pitch on the substrate, the first and second periodic arrays having different structures, and wherein the first pitch is different from that of the second pitch, wherein the first periodic array of structures is interlaced with the second periodic array of structures, wherein a feature of the first periodic array of structures is different from the same feature of the second array of structures, wherein an effective pitch of the interlaced arrays is determined wherein only the first pitch is comparable to a wavelength of a measurement radiation beam, and wherein the effective pitch remains constant if the first periodic array of structures is misaligned on the substrate in relationship to the second periodic array of structures, the projection system configured to print the same overlay target onto a subsequent layer of the substrate;

a detector configured to detect radiation redirected from the overlay targets; and a processor configured to determine whether there is an overlay error from the detected redirected radiation.

* * * * *